US00PP29108P2

(12) United States Plant Patent
Smith

(10) Patent No.: US PP29,108 P2
(45) Date of Patent: Mar. 13, 2018

(54) ***CHRYSANTHEMUM* PLANT NAMED 'CIFZ0046'**

(50) Latin Name: *Chrysanthemum×morifolium*
Varietal Denomination: CIFZ0046

(71) Applicant: SYNGENTA PARTICIPATIONS AG, Basel (CH)

(72) Inventor: Mark A. Smith, Alva, FL (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/530,544

(22) Filed: Jan. 26, 2017

(51) Int. Cl.
*A01H 5/02* (2006.01)

(52) U.S. Cl.
USPC ..... Plt./290

(58) Field of Classification Search
USPC ..... Plt./290
CPC ..... A01H 5/0255
See application file for complete search history.

*Primary Examiner* — Kent L Bell
(74) *Attorney, Agent, or Firm* — Dale Skalla

(57) ABSTRACT

A new garden type *Chrysanthemum* plant named 'CIFZ0046' particularly distinguished by the small (1.5 inch) orange two-tone decorative inflorescence, a medium sized plant with round mound habit and a natural season response in early October.

1 Drawing Sheet

Figure 1:
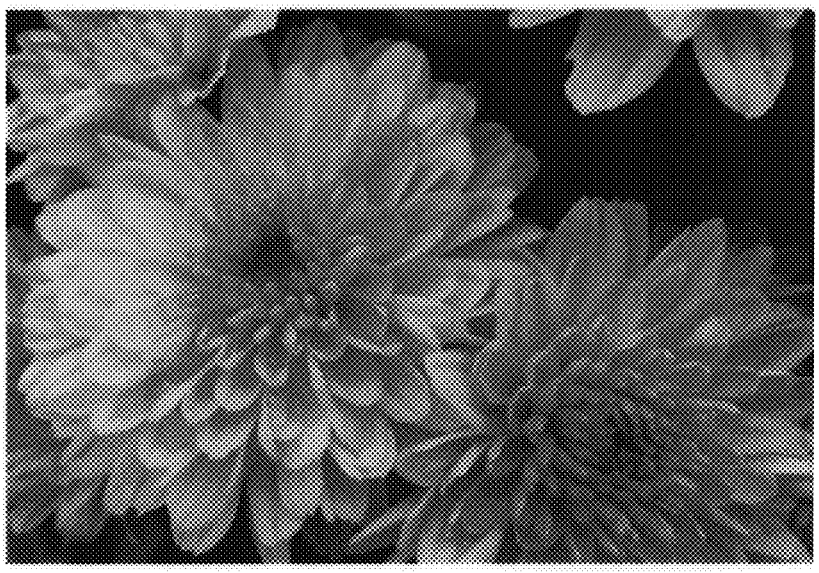

Latin name of the genus and species of the plant claimed: *Chrysanthemum×morifolium.*

Varietal denomination: 'CIFZ0046'.

BACKGROUND OF THE NEW PLANT

The present invention comprises a new *Chrysanthemum*, botanically known as *Chrysanthemum×morifolium*, and hereinafter referred to by the variety name 'CIFZ0046'.

'CIFZ0046' is a product of a planned breeding program. The new cultivar has small (1.5 inch) orange two-tone decorative inflorescence, a medium sized plant with round mound habit and a natural season response in early October.

'CIFZ0046' originated from a cross made in November 2008 in Tenjo, Columbia The female parent was 'Zanmuflamin', U.S. Plant Pat. No. 20,589, commercially known as 'Flamingo Pink'.

When compared to the female parent, 'CIFZ0046' has:

1. Similar flower type and size but orange two-tone inflorescence color not lavender-coral like 'Flamingo Pink'.
2. Blackcloth response is one week faster and natural season response is ten days slower than 'Flamingo Pink'.
3. Similar plant size and similar plant habit as 'Flamingo Pink'.

The male parent was the light yellow unnamed seedling from own breeding '05-M263'.

When compared to the male parent, 'CIFZ0046' has:

1. Smaller flower size with less disc florets and inflorescence color is darker/more orange with two-tone contrast unlike the light yellow of the male parent.
2. Blackcloth response is a half a week slower and natural season response is one month slower than the male parent.
3. Similar plant habit but larger overall size than the male parent.

The resultant seed was sown in June 2011 in Gilroy, Calif.

The first act of asexual reproduction of 'CIFZ0046' was accomplished when vegetative cuttings were propagated from the initial selection, this initial selection took place in Nov. 1, 2011 in Monroeville, N.J.

BRIEF SUMMARY OF INVENTION

Horticultural examination of plants grown from cuttings of the plant initiated in January 2012 in Monroeville, N.J., and continuing thereafter, has demonstrated that the combination of characteristics as herein disclosed for 'CIFZ0046' are firmly fixed and are retained through successive generations of asexual reproduction.

'CIFZ0046' has not been observed under all possible environmental conditions. The phenotype may vary significantly with variations in environment such as temperature, light intensity and day length.

'CIFZ0046' has not been made publicly available prior to the effective filing date of this application, notwithstanding any disclosure that may have been made less than one year prior to the effective filing date of this application by the inventor or another who obtained 'CIFZ0046' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical inflorescence and foliage characteristics of 'CIFZ0046' with colors being as true as possible with an illustration of this type. The photographic drawing shows in FIG. 1 a close view of the inflorescences of the new variety and in FIG. 2 a flowering plant from an outdoor trial.

Figure 2:
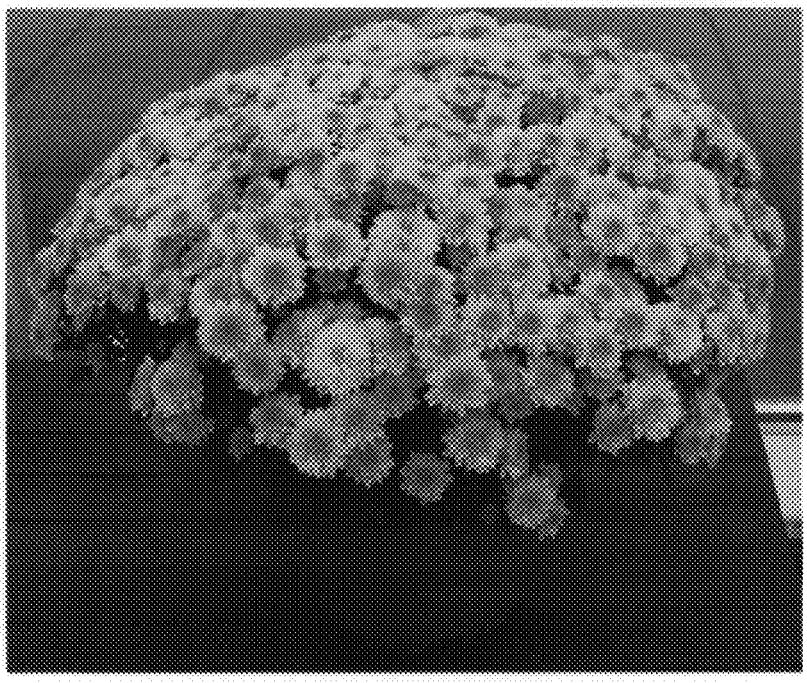

The aforementioned photographs: FIG. 1, as well as FIG. 2, were taken on Sep. 5, 2016 both showing a plant from the same blackcloth outdoor trial in Enkhuizen, the Netherlands.

These plants were about 13 weeks of age. One rooted cutting per pot had been planted in a 19 cm pot in week 23, not pinched. Shortday blackcloth treatment was applied from week 29 on. Plants started flowering late August.

DETAILED BOTANICAL DESCRIPTION

The measurements were taken in Enkhuizen, The Netherlands on Sep. 5, 2016 on the plants from the trial mentioned afore.

Color references are made to The Royal Horticultural Society Colour Chart (R.H.S.) 2001.

TABLE 1DIFFERENCES BETWEEN THE NEW VARIETY 'CIFZ0046' AND TWO MOST SIMILAR VARIETIES:

| | 'CIFZ0046' | 'Yoashley', U.S. Pat. No. PP18,916 |
|---|---|---|
| Flowering response (blackcloth): | Similar | Similar |
| Flowering response (natural): | Half a week slower except in south US where it is a half a week faster than 'Yoashley' | Half a week faster except in south US where it is a half a week slower than 'CIFZ0046' |
| Flowering uniformity: | More uniform | Less uniform |
| Inflorescence color: | Two-tone contrast | No two-tone contrast |
| Inflorescence size: | Similar | Similar |
| Plants, stems, flexibility: | Greater width | More oval plant shape |

| | 'CIFZ0046' | 'Conaco Orange', Not patented |
|---|---|---|
| Flowering response (blackcloth): | One week faster | One week slower |
| Flowering response (natural): | Half a week slower | Half a week faster |
| Flowering longevity: | Longer lasting flowers | Shorter lasting flowers |
| Inflorescence color: | Lighter inflorescence color | Darker inflorescence color |
| Inflorescence size: | Smaller inflorescence | Bigger inflorescence |

Plant:

*Form, growth and habit.*—Herbaceous garden-type, stems upright and outwardly spreading, freely branching, strong and moderately vigorous growth habit.

*Plant height (above soil).*—20-22 cm.

*Plant height (inflorescence included).*—21-25 cm.

*Plant width.*—39-41 cm.

Roots:

*Number of days to initiate roots.*—About 4 days at about 22 degrees C.

*Number of days to produce a rooted cutting.*—14 days at 22 degrees C.

*Type.*—Fine, fibrous, free branching.

*Color.*—RHS N165A.

Foliage:

*Arrangement.*—Alternate.

*Immature leaf, color upper surface.*—RHS 139A.

*Immature leaf, color lower surface.*—RHS 137B.

*Mature leaf, color, upper surface.*—RHS 139A.

*Mature leaf, color lower surface.*—RHS 137B.

*Length.*—6.8-8.7 cm.

*Width.*—4.5-5.4 cm.

*Shape.*—Ovate, with distinct lobes.

*Base shape.*—Attenuate.

*Apex shape.*—Acute.

*Margin.*—5-lobed (palmate), edge dentate.

*Texture, upper surface.*—Short hairs, more dense at veins.

*Texture, lower surface.*—Short hairs.

*Color of veins, upper surface.*—RHS 137A.

*Color of veins, lower surface.*—RHS 137B.

*Pattern of veining.*—Palmate to reticulate.

*Petiole color.*—RHS 137A.

*Petiole length.*—1.5 cm.

*Diameter.*—0.4 cm.

*Texture.*—Densely covered with short hairs.

Stem:

*Quantity of main branches per plant.*—9-11.

*Color of stem.*—RHS 152A at bases to RHS 146B at top.

*Length of stem.*—20 cm.

*Diameter.*—0.5 cm.

*Length of internodes.*—0.9-2.0 cm.

*Texture.*—Densely covered with short hairs.

*Color of peduncle.*—RHS 146B.

*Length of peduncle.*—2.5 to 5 cm.

*Peduncle diameter.*—0.2 cm.

*Texture.*—Densely covered with short hairs.

Inflorescence:

*Type.*—Compositae, solitary, decorative-type inflorescences borne terminally above foliage, praemorse tipped ray florets arranged acropetally on a capitulum.

*Quantity of short days to flowering (response time).*—Approximately six weeks.

*Natural season flowering.*—Early October.

*Quantity of inflorescences per plant.*—300-500.

*Lastingness of individual blooms on the plant.*—About five weeks from first color.

*Fragrance.*—Slightly spicy.

Bud (when showing color):

*Color.*—RHS 169A.

*Length.*—1.0 cm.

*Width.*—0.7 cm.

*Shape.*—Oblate.

Immature inflorescence:

*Diameter.*—5.0-6.0 cm.

*Color of ray florets, upper surface.*—Darker than RHS N34A.

*Color of ray florets, lower surface.*—Close to RHS 22A.

Mature inflorescence:

*Diameter.*—3.5-4.2 cm.

*Depth.*—1-1.3 cm.

*Total diameter of disc.*—0-0.4 cm.

*Receptacle color.*—RHS 146B.

*Receptacle height.*—0.3-0.4 cm.

*Receptacle diameter.*—1.2 cm.

Ray florets:

*Average quantity of florets.*—Between 140 and 150 in several whorls.

*Color of florets, upper surface (abaxial).*—RHS 34A; fading to RHS 12A when turning old.

*Color inner surface (adaxial).*—RHS 11A with stripes RHS 22A.

*Length.*—1.6-2.0 cm.

*Width/diameter.*—0.7 cm; 0.2 cm for the tube at the base.

*Shape.*—Obtuse.

*Apex shape.*—Praemorse.

*Base shape*.—Tube.
*Margin*.—Entire.
*Texture, upper surface*.—Papillate.
*Lower surface*.—Papillate.

Disc florets:
*Average quantity of florets*.—20.
*Color of florets*.—RHS 21B.
*Length*.—0.4 cm.
*Width*.—0.15 cm.
*Shape*.—Tubular, elongated.
*Apex shape*.—Acute, 5 pointed.

Phyllaries:
*Quantity*.—20-25 in 2-3 whorls.
*Color, upper surface*.—RHS 146B.
*Color, lower surface*.—RHS 146B.
*Length*.—0.5-0.8 cm.
*Width*.—0.2-0.3 cm.
*Shape*.—Lanceolate.
*Apex shape*.—Acute.
*Base*.—Fused.
*Margins*.—Entire.
*Texture, upper surface*.—Glabrous, a few tiny hairs.
*Texture, lower surface*.—Densely covered with short hairs.

Reproductive organs:
*Pistil*.—One.
*Length*.—0.3 cm.
*Style color*.—RHS 150B.
*Style length*.—0.3 cm.
*Stigma color*.—RHS 6B.
*Stigma shape*.—Bi-parted.
*Ovary color*.—RHS 150D.
*Ovary length*.—0.2 cm.
*Ovary width*.—0.1 cm.

Androecium:
*Stamens*.—1, found on only disc florets.
*Color of filaments*.—RHS 2B, 140D at base.
*Length filaments*.—0.15-0.2 cm.
*Anther color*.—RHS 13A.
*Anther length*.—0.15-0.2 cm.
*Anther shape*.—Oval to club shaped.
*Color of pollen*.—RHS 13A.
*Pollen amount*.—Moderate.
*Fertility/seed set*.—Has not been determined to date.
*Disease/pest resistance*.—Has not been determined to date.

What is claimed is:

1. A new and distinct variety of *Chrysanthemum* plant named 'CIFZ0046' substantially as illustrated and described herein.

* * * * *